United States Patent
Wedlin et al.

(10) Patent No.: US 10,172,978 B2
(45) Date of Patent: Jan. 8, 2019

(54) MEDICAL DEVICE FOR SHORT TIME USE WITH QUICKLY RELEASABLE ANTIBACTERIAL AGENT

(75) Inventors: Charlotte Wedlin, Mölndal (SE); Eva-Helena Maj Westman, Stockholm (SE); Johan Per Lundahl, Målsryd (SE)

(73) Assignee: ASTRA TECH AB, Mölndal (SE)

( * ) Notice: Subject to any disclaimer, the term of this patent is extended or adjusted under 35 U.S.C. 154(b) by 0 days.

(21) Appl. No.: 12/971,123

(22) Filed: Dec. 17, 2010

(65) Prior Publication Data

US 2011/0152843 A1    Jun. 23, 2011

Related U.S. Application Data

(60) Provisional application No. 61/288,074, filed on Dec. 18, 2009.

(30) Foreign Application Priority Data

Dec. 18, 2009 (EP) .................................... 09180019

(51) Int. Cl.
*A61M 25/00* (2006.01)
*A61L 31/02* (2006.01)
*A61L 31/12* (2006.01)
*A61L 29/16* (2006.01)
*A61L 29/08* (2006.01)
*A61L 29/14* (2006.01)
*A61L 31/14* (2006.01)
*A61L 31/16* (2006.01)

(52) U.S. Cl.
CPC ............. *A61L 29/16* (2013.01); *A61L 29/085* (2013.01); *A61L 29/14* (2013.01); *A61L 31/14* (2013.01); *A61L 31/16* (2013.01); *A61L 2300/104* (2013.01); *A61L 2300/404* (2013.01)

(58) Field of Classification Search
CPC ........ A01N 25/04; A01N 25/10; A01N 25/34; A01N 59/16; A61L 2/238; A61L 27/54; A61L 29/08; A61L 29/085; A61L 29/14; A61L 29/16; A61L 31/10; A61L 31/14; A61L 31/16; A61L 2300/102; A61L 2300/104; A61L 2300/404; A61L 2300/602; A61L 2300/606; A61L 2300/62; A61M 2025/0056; C08K 3/08; C08L 2666/04; C08L 2666/54; C08L 27/06; C09D 175/08; Y10T 428/31551; Y10T 428/31609; Y10T 428/31663
USPC .... 427/2.28, 379, 385.5, 386, 387; 523/122; 524/398–400, 403, 413, 430–437; 604/265, 544

See application file for complete search history.

(56) References Cited

U.S. PATENT DOCUMENTS

| | | | |
|---|---|---|---|
| 4,666,437 A | 5/1987 | Lambert | |
| 4,769,013 A * | 9/1988 | Lorenz | A61L 15/225 106/18.24 |
| 5,395,651 A | 3/1995 | Sodervall et al. | |
| 5,470,585 A * | 11/1995 | Gilchrist | A01N 25/08 424/409 |
| 5,747,178 A | 5/1998 | Sodervall et al. | |
| 6,716,444 B1 * | 4/2004 | Castro | A61L 27/306 424/400 |
| 7,378,156 B2 | 5/2008 | Terry | |
| 2001/0055622 A1 * | 12/2001 | Burrell | A61K 33/24 424/600 |
| 2002/0018795 A1 * | 2/2002 | Whitbourne | A61K 9/0024 424/414 |
| 2003/0118664 A1 * | 6/2003 | Trogolo | A01N 25/26 424/618 |
| 2004/0106912 A1 * | 6/2004 | Rosinskaya | A61L 29/085 604/500 |
| 2005/0013842 A1 * | 1/2005 | Qiu | A61L 12/088 424/423 |
| 2006/0216327 A1 * | 9/2006 | Madsen | A61L 27/34 424/426 |
| 2006/0240069 A1 | 10/2006 | Utas et al. | |
| 2006/0263404 A1 * | 11/2006 | Nielsen | A61L 29/085 424/422 |
| 2007/0003603 A1 * | 1/2007 | Karandikar | A01N 59/16 424/443 |
| 2007/0016169 A1 * | 1/2007 | Utas | A61L 29/14 604/544 |
| 2007/0218298 A1 | 9/2007 | Terry | |
| 2007/0299518 A1 * | 12/2007 | Ruane | A61L 27/34 623/11.11 |
| 2008/0131606 A1 * | 6/2008 | Trogolo | A01N 25/34 427/385.5 |
| 2008/0181931 A1 * | 7/2008 | Qiu | A61L 12/088 424/429 |

(Continued)

FOREIGN PATENT DOCUMENTS

| CN | 1434729 A | 8/2003 |
|---|---|---|
| CN | 101255274 A | 9/2008 |

(Continued)

OTHER PUBLICATIONS

European Search Report: EP 09 18 0019.

(Continued)

*Primary Examiner* — Adam Marcetich
(74) *Attorney, Agent, or Firm* — Ladas & Parry LLP; Loren K. Thompson

(57) ABSTRACT

A method is presented for providing a medical device with antibacterial activity, whereby a substrate material coated with a hydrophilic polymer is provided, the hydrophilic polymer exhibiting a low friction when wetted; also provided is a colloidal solution comprising chemically reduced particles of an oligodynamic metal and a hydrophilic polymer, the hydrophilic polymer being the same as in the coating of the substrate material; and the step of dipping the substrate material in the solution. A medical device prepared accordingly is also provided.

15 Claims, No Drawings

(56) References Cited

U.S. PATENT DOCUMENTS

| | | | |
|---|---|---|---|
| 2008/0200907 A1* | 8/2008 | Nestenborg | A61M 25/002 604/544 |
| 2008/0241218 A1* | 10/2008 | McMorrow | A61F 2/915 424/426 |
| 2008/0317813 A1* | 12/2008 | Craig | A61L 31/10 424/423 |
| 2009/0005862 A1* | 1/2009 | Nakatani | A61F 2/91 623/1.49 |
| 2009/0035341 A1* | 2/2009 | Wagener | A01N 25/34 424/409 |
| 2009/0092538 A1* | 4/2009 | Khanolkar | G02B 1/043 423/491 |
| 2009/0253826 A1* | 10/2009 | Kocher et al. | 523/122 |
| 2009/0324738 A1* | 12/2009 | Krongauz | A61L 29/085 424/618 |
| 2010/0015206 A1* | 1/2010 | Flanagan | A61L 31/088 424/426 |
| 2010/0086580 A1* | 4/2010 | Nyman | A61L 27/34 424/423 |
| 2010/0150989 A1* | 6/2010 | Hoffman | A61K 9/0024 424/445 |
| 2011/0014258 A1* | 1/2011 | Gan | A61L 27/30 424/409 |
| 2011/0059874 A1* | 3/2011 | Rooijmans | C08F 2/50 508/100 |
| 2011/0135735 A1* | 6/2011 | Steinruecke | A01N 59/00 424/489 |

FOREIGN PATENT DOCUMENTS

| | | |
|---|---|---|
| EP | 0 093 093 A1 | 11/1983 |
| EP | 0 217 771 A1 | 4/1987 |
| EP | 1 688 470 A1 | 8/2006 |
| JP | 2002535090 A | 10/2002 |
| JP | 2003529630 A | 10/2003 |
| WO | 98/58989 A1 | 12/1998 |
| WO | 00/09173 A1 | 2/2000 |
| WO | 00/30696 A1 | 6/2000 |
| WO | 00444414 A1 | 8/2000 |
| WO | 01/43788 A2 | 6/2001 |
| WO | 0143788 A2 | 6/2001 |
| WO | 2007/067794 A1 | 6/2007 |
| WO | 2009012336 A1 | 1/2009 |

OTHER PUBLICATIONS

Extended European Search Report; dated Jun. 7, 2013; Appln. No. 12178600.0-1455 /2543399.

Yuan Yguerabide, et al; "Light-Scattering Submicroscopic Particles as Highly Fluorescent Analogs and Their Use as Tracer Labels in Clinical and Biological Applications," Analytical Biochemistry Sep. 10, 1998, 262(2): pp. 137-156.

\* cited by examiner

MEDICAL DEVICE FOR SHORT TIME USE WITH QUICKLY RELEASABLE ANTIBACTERIAL AGENT

FIELD OF THE INVENTION

The present invention relates to a medical device comprising a substrate material and a hydrophilic surface coating arranged on at least a part of the surface of said substrate material. The medical device further comprises an antibacterial agent, and provides an efficient release of said antibacterial agent. Further, the invention relates to a method for the production of such a medical device.

BACKGROUND OF THE INVENTION

It is known to coat medical devices, e.g. catheters for introduction into human cavities such as blood vessels, digestive organs and the urinary system, with a hydrophilic coating, at least on the surface of the insertable part which is introduced or comes into contact with mucous membranes, etc., during introduction of the device. An advantage with such a hydrophilic coating is that it becomes extremely slippery when it is swelled with water, preferably immediately before introduction into the human body and thus ensures a substantially painless introduction with a minimum of damage on tissue.

A large number of methods are known for the production of hydrophilic surface coatings. A known hydrophilic coating process is e.g. disclosed in EP 0 093 093, where isocyanate is used to form a polyurea network for connecting hydrophilic PVP to the substrate. Further, EP 0 217 771 describes a method of adding an osmolality increasing compound to such a hydrophilic coating in order to improve the water retention properties and low friction of the coating. Further, WO 98/58989 discloses a hydrophilic coating which is cross-linked by means of irradiation, and incorporating a water soluble osmolality increasing compound therein.

However, despite adherence to sterile guidelines etc, the use of medical devices, and in particular introduction of medical devices into natural and artificial body openings, implies a risk of bacterial contamination. For example, insertion and maintenance of urinary catheters poses a problem in relation to catheter-associated infections. When medical devices such as a catheter is introduced into the human cavity, the normal human defense barrier may be penetrated, which can result in introduction of bacteria, fungi, vira, or tissue-like or multiple organized cells. Urinary tract infection (UTI), for instance, is a problem associated with the use of urinary catheters, including hydrophilic catheters with hydrophilic coatings for intermittent use. It is estimated that almost one-quarter of hospitalized spinal cord-injured patients develop symptomatic UTI during their hospital course. Gram-negative bacilli account for almost 60-70%, enterococci for about 25% and *Candida* species for about 10% of cases of UTI. It is well known that persons practicing intermittent urethral catheterization as a daily routine often have problems with symptomatic UTI.

To this end, and in order to maintain sterility and cleanness of the medical device, medical devices, such as urinary catheters, may be coated with an antimicrobial compound for prevention of bacterial infection. US 2006/0240069, for instance, discloses a use of at least one salt of organic acid(s), and preferably a benzoate or a sorbate, as an antimicrobial agent. Further, WO 00/09173 discloses a stabilized composition having antibacterial, antiviral and/or antifungal activity characterized in that it comprises a silver compound. Light stabilized silver composition can be introduced into catheters or similar medical devices.

For many years silver and silver salts have been used as antimicrobial agents. Silver salts, colloids, and complexes have also been used to prevent and to control infection. For example, colloidal metallic silver has been used topically for conjunctivitis, urethritis, and vaginitis. Other metals, such as gold, zinc, copper, and cerium, have also been found to possess antimicrobial properties, both alone and in combination with silver. These and other metals have been shown to provide antimicrobial behavior even in minute quantities, a property referred to as "oligodynamic."

Other examples of medical devices having a hydrophilic coating, and an antimicrobial composition such as silver arranged as a separate layer or introduced into the hydrophilic layer, are disclosed in U.S. Pat. No. 7,378,156 and in EP 1 688 470.

However, a problem with known methods of using oligodynamic metals as antimicrobial and antibacterial agent in medical devices is that it is difficult to control the release of the oligodynamic metal ions. If the release rate is too low, the antibacterial properties would be inadequate, and at the same time a too high release rate may be uncomfortable and even harmful for the patient, and also results in a more costly product. In addition, a too high release rate may result in a substantial loss of oligodynamic compound in the wetting solution, again leading to inadequate antibacterial properties in the intended use situation. Accordingly, there is a need for an improved medical device of the above-discussed type, where the release rate of the oligodynamic metal ions can be controlled more accurately.

SUMMARY OF THE INVENTION

It is therefore an object of the present invention to provide a medical device and a method for producing such a medical device, enabling an improved control of the release rate of an antimicrobial or antibacterial agent, and thereby alleviating the above-discussed problems of the previously known solutions.

This object is achieved with a medical device and a method according to the appended claims.

According to a first aspect of the invention there is provided a method for providing a medical device with antibacterial activity, comprising the steps of:

providing a substrate material coated with a hydrophilic polymer, said hydrophilic polymer exhibiting a low friction when wetted;

providing a colloidal solution comprising chemically reduced particles of an oligodynamic metal and a hydrophilic polymer, said hydrophilic polymer being the same as in the coating of the substrate material; and dipping said substrate material in the solution.

It has surprisingly been found by the present inventors that by dipping the coated substrate in a colloidal solution comprising chemically reduced particles of an oligodynamic metal and a hydrophilic polymer, wherein the hydrophilic polymer is the same as in the coating of the substrate material, a high concentration of colloidal particles of the oligodynamic metal and the hydrophilic polymer is obtained in the coating. Further, it has been found that the release of said particles when the coating is in a wetted state in subsequent use of the medical device, such as when a urinary catheter is inserted into the urethra, is very efficient, allowing a substantial part of the particles to be released in a relatively short time. Hereby, a substantial part of the particles are released and actively working as antibacterial agents. The released particles also continue to be active for a substantial time after the release. Hereby, when used in e.g. urinary catheters for intermittent catheterization, the released particles will remain in the urethra and the bladder even when the urinary catheter is withdrawn, and consequently provide an antibacterial effect also between catheterizations.

Hereby, it becomes possible to effectively tailor the antibacterial properties of the medical device for the intended use, and optimize the antibacterial effect and at the same time effectively preventing any excessive release of antibacterial ions, which may be harmful for the patient.

Without the intention to be bound to any theories, it is assumed that the reason for the very efficient release of silver from the medical device according to the present invention is at least partly due to the very large contact surface area being provided by the small colloidal particles, and relative loose bond holding the particles to the coating of the medical device.

The hydrophilic polymer in the colloidal solution functions as a stabilization agent, limiting the growth of the colloidal particles to a desired size. Further, the resulting colloidal particles will comprise the hydrophilic polymer. It is assumed that the hydrophilic polymer hereby forms an outer layer on the particles, i.e. like an encapsulation of the metallic inner content. The inclusion of hydrophilic polymer onto the colloidal particles also provides a very good adherence to the hydrophilic coating of the medical device, at the same time providing a high concentration of colloidal particles in the coating after dipping, and also a relatively loose connection between the particles and the coating, enabling a fast a reliable release of the particles and ions during subsequent use.

By "colloidal solution" is in the context of this application understood a solution in which the particles are present in such a small grain size that they dispersed evenly throughout the solvent and maintain a homogeneous appearance. However, the particles of the dispersed substance are only suspended in the mixture, unlike in a solution, in which they are completely dissolved. The "colloidal solution" may also be referred to as a ""colloidal system". The colloid particles preferably have a diameter of between approximately 1 and 200 nanometers. Such particles are normally invisible to an optical microscope, though their presence can be confirmed indirectly from light scattering or with the use of an ultramicroscope or an electron microscope.

By "oligodynamic metals" are in this application meant any metal that has antimicrobial or antibacterial behavior even in minute quantities. Examples of such oligodynamic metals are silver, e.g. in the form of silver salts, colloids, and complexes, and other metals, such as gold, zinc, copper, and cerium.

The oligodynamic metal of the antibacterial layer preferably comprises silver. Silver ions have a well-documented and effective antibacterial effect, and have also been found to be adequately controllable by means of an upper hydrophilic layer of a suitable thickness. Since the particles comprise crystallized silver, the release of silver ions from the particles will continue for a substantial time after the release of the particles.

The hydrophilic polymer of the hydrophilic surface coating is preferably at least one of: polyvinyl compounds, polylactames, in particular such as polyvinyl pyrrolidones, polysaccharides, in particular heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride. Preferably the hydrophilic surface coating comprises a hydrophilic polymer which obtains a significantly lowered surface friction when wetted with a wetting liquid. Most preferably, the hydrophilic surface coating comprises polyvinylpyrrolidone (PVP).

The provision of the colloidal solution preferably comprises mixing an oligodynamic metal salt in a solvent together with a reducing agent and the hydrophilic polymer.

When the oligodynamic metal is silver, the oligodynamic metal salt is preferably selected from the group consisting of $AgNO_3$, $CH_3CO_2Ag$, $CH_3CH(OH)CO_2Ag$, $AgClO_4$, $AgSO_4$, $Ag_2O_3$, $AgBF_4$, $AgIO_3$, $AgCl$, $AgI$ and $AgBr$. Most preferably, the oligodynamic metal salt is silver nitrate.

The solvent is preferably water and/or ethanol. Most preferably, the solvent is water, because it is easy to use and leaves no harmful residues etc, and is also very cost efficient. However, alternative solvents are also feasible, such as methanol or methylene chloride.

The reducing agent is preferably selected from the group consisting of boranes, copper hydride, diborane, diisobutylaluminium hydride, ascorbic acid, dimethylsulfide borane, formaldehyde, formic acid, hydrazine, isopropanol, lithium aluminum hydride, lithium tetrahydridoaluminate, nickel, nickel borohydride, oxalyc acid, polymethylhydrosiloxane, sodium bis(2-methoxyethoxy)aluminumhydride, sodium borohydride, sodium cyanoborohydride, sodium hydrosulfite, sodium tetrahydroborate, sodium triacetoxyborohydride, tributylstannane, tributyltin hydride, trichlorosilane, triphenylphosphine, triphenylphosphite, triethylsilane, tris(trimethylsilyl)silane and sodium borohydride. Most preferably, the reducing agent is ascorbic acid.

The hydrophilic polymer is preferably at least one of: polyvinyl compounds, polylactames, in particular such as polyvinyl pyrrolidones, polysaccharides, in particular heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride. Most preferably, the hydrophilic polymer is polyvinyl pyrrolidone.

The hydrophilic coating preferably forms a polyurea network, and most preferably the polyurea network is arranged to form a covalent bond to active hydrogen groups in the substrate. Alternatively, the hydrophilic coating may form an ester bond or an epoxy bond to active hydrogen groups in the substrate.

According to one embodiment, coating of the substrate material may be made by a process comprising the steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

However, other hydrophilic coatings are also feasible, such as a coating comprising hydrophilic polymers cross-linked directly to the substrate. The cross-linking may be effected by means of irradiation, e.g. by electron beams or UV light.

The present invention is particularly suitable for the catheters, and specifically urinary catheters, and most preferably for urinary catheters for intermittent, short time use. The term "short term use" indicates a use that is limited in time, and in particular limited to a time period of less than 15 minutes, and preferably less than 10 minutes, and most preferably less than 5 minutes.

However, the production method is also useful for many other types of medical devices having a hydrophilic coating. Accordingly, the method according to the present invention is not limited to urinary catheters. Examples of such other medical devices for which the present invention is useful are vascular catheters and other types of catheters, endo and laryngoscopes, tubes for feeding, or drainage or endotracheal use, condoms, wound dressings, contact lenses, implants, extracorporeal blood conduits, membranes e.g. for dialysis, blood filters and devices for circulatory assistance.

The present invention is useable for a large variety of different substrate materials. However, preferably the substrate is made of a polymer material. The substrate may e.g. comprise at least one of: polyurethanes, latex rubbers, silicon rubbers, other rubbers, polyvinylchloride (PVC), other vinyl polymers, polyesters, polyacrylates, polyamides, polyolefines, thermoplastic elastomers, styrene block copolymers (SBS), or polyether block amid (PEBA).

The coating solution may further comprise a dissolved osmolality increasing compound, such as sodium chloride. Other osmolality increasing compounds, such as urea and the osmolality increasing compounds discussed in EP 0 217 771 are also feasible, said document hereby incorporated by reference. Additionally or alternatively, it is also possible to provide the osmolality increasing compound in the wetting fluid.

According to another aspect of the present invention, there is provided a medical device with antibacterial activity, comprising a substrate material and a hydrophilic polymer surface coating arranged on at least a part of the surface of said substrate material, said hydrophilic polymer exhibiting a low friction when wetted, wherein said coating further comprises colloidal particles of an oligodynamic metal and a hydrophilic polymer, said hydrophilic polymer being the same as in the coating of the substrate material.

By means of the latter aspects of the invention, similar advantages and specific embodiments as discussed in respect of the first discussed aspect and embodiments are obtainable.

These and other aspects of the invention will be apparent from and elicidated with reference to the embodiments described hereinafter.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. The hydrophilic medical devices may be used for many different purposes, and for insertion into various types of body-cavities. However, the following discussion is in particular concerned with the preferred field of use, urinary catheters, even though the invention is not limited to this particular type of catheters or even this particular type of medical device. It is to be appreciated by those skilled in the art that the inventive concept is not limited to any certain type of devices, but could be used different types of medical devices.

In case of catheters, at least a part of an elongate tube forms an insertable length to be inserted through a body opening of the user, such as the urethra in case of a urinary catheter. By insertable length is normally, in the context of a hydrophilic catheter, meant that length of the elongate tube which is coated with a hydrophilic material, for example PVP, and which is insertable into the urethra of the patient. Typically, this will be 80-140 mm for a female patient and 200-350 mm for a male patient.

The elongate shaft/tube of the catheter is made of a substrate material. The substrates may be made from any polymer material, which are well-known in the technical field and to which the said hydrophilic polymers adhere, such as polyurethanes, latex rubbers, other rubbers, polyvinylchloride, other vinyl polymers, polyesters and polyacrylates. However, preferably the substrate is made of a polymer blend comprising a polyolefin and a composition having molecules with active hydrogen groups, and preferably a composition having molecules with active hydrogen groups. The polyolefin can comprise at least one polymer selected from the group: polyethene, polypropene, and styrene block copolymer (SBS). The composition having molecules with active hydrogen groups can be a polymer having active hydrogen groups bound to the polymer via nitrogen, such as polyamide or polyurethane.

A hydrophilic coating is arranged on at least part of the substrate forming the catheter shaft, and on top of the above-discussed antibacterial coating layer. The hydrophilic polymer coating may comprise material selected from polyvinyl compounds, polysaccharides, polyurethanes, polyacrylates or copolymers of vinyl compounds and acrylates or anhydrides, especially polyethyleneoxide, polyvinylpyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleic acid anyhydride. The preferred hydrophilic polymer is polyvinylpyrrolidone.

A preferred method for coating of the substrate will now be disclosed in more detail. The outer surface of the elongate shaft is preferably coated with a stable hydrophilic coating by applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature. The isocyanate solution may advantageously contain between 0.5 to 10% (weight to volume) of the isocyanate compound, and may preferably contain between 1 to 6% (weight to volume) of the isocyanate compound. Generally, the isocyanate solution only needs to be in contact with the surface briefly, for example 5 to 60 sec.

Application of the isocyanate solution to the substrate surface results in a coating having unreacted isocyanate groups being formed on the substrate surface. Application of the polyvinylpyrrolidone solution to the substrate surface then results in a hydrophilic polyvinylpyrrolidone-polyurea interpolymer coating being formed. Curing of this hydrophilic coating binds the isocyanate compounds together to form a stable non-reactive network that binds the hydrophilic polyvinylpyrrolidone. To advantage, curing takes place in the presence of a water-containing gas, for example ambient air, to enable the isocyanate groups to react with the water to yield an amine which rapidly reacts with other isocyanate groups to form a urea cross-link. Further, the method may comprise the steps of evaporating the solvent of the isocyanate solution prior to application of the polyvinylpyrrolidone solution and evaporating the solvent of the polyvinylpyrrolidone solution prior to curing of the hydrophilic coating. This may for example be done by air drying.

The isocyanate compound preferably comprises at least two unreacted isocyanate groups per molecule. The isocyanate may be selected from 2,4-toluene diisocyanate and 4,4'-diphenylmethane diisocyanate, or a pentamer of hexamethylene diisocyanate and toluene diisocyanate of cyanurate type, or trimerized hexamethylene diisocyanate biuret or mixtures thereof.

The solvent for the isocyanate compound is preferably one which does not react with isocyanate groups. The preferred solvent is methylene chloride but it is also possible to use ethyl acetate, acetone, chloroform, methyl ethyl ketone and ethylene dichloride, for example.

In order to shorten the necessary reaction times and curing times suitable catalysts for isocyanate curing may be added. These catalysts may be dissolved in either the isocyanate solution or the polyvinylpyrrolidone solution but are preferably dissolved in the latter. Different types of amines are especially useful, for example diamines, but also for example triethylenediamine. Preferably, an aliphatic amine is employed which is volatisable at the drying and curing temperatures used for the coating, and which furthermore is non-toxic. Examples of suitable amines are N,N' diethylethylendiamine, hexamethylendiamine, ethylendiamine, para-diaminobenzene, 1,3-propandiol-para-aminobenzoic acid diester and diaminobicyclo-octane.

The polyvinylpyrrolidone used preferably has a mean molecular weight of between 104 to 107 with the most preferred mean molecular weight being about 105. Polyvinylpyrrolidone having such a molecular weight is commercially available, for example under the trademark Kollidon® (BASF). Examples of suitable solvents for polyvinylpyrrolidone that may be used are methylene chloride (preferred), ethyl acetate, acetone, chloroform, methyl ethyl ketone and ethylene dichloride. The proportion of polyvinylpyrrolidone in the solution is preferably between 0.5 to 10% (weight to volume) and most preferred between 2 to 8% (weight to volume). The polyvinylpyrrolidone in the solvent is applied by dipping, spraying or the like for a short period of time, e.g. during 5 to 50 sec.

Curing of the coating is preferably performed at a temperature of 50 to 130 deg. C., in for example an oven, for a duration of between 5 to 300 min.

However, it is also feasible to use other types of hydrophilic coatings, such as coatings cross-linked by means of UV or e-beam radiation.

Colloidal particles including an oligodynamic metal, preferably silver, and the same hydrophilic polymer as in the coating are further incorporated into the coating. Preferably, these colloidal particles are introduced after forming of the coating on the substrate, and most preferably by means of dipping the coated medical device in a colloidal solution.

The colloidal solution is preferably prepared by mixing an oligodynamic metal salt in a solvent together with a reducing agent and the hydrophilic polymer.

When the oligodynamic metal is silver, the oligodynamic metal salt is preferably selected from the group consisting of $AgNO_3$, $CH_3CO_2Ag$, $CH_3CH(OH)CO_2Ag$, $AgClO_4$, $AgSO_4$, $Ag_2O_3$, $AgBF_4$, $AgIO_3$, $AgCl$, $AgI$ and $AgBr$. Most preferably, the oligodynamic metal salt is silver nitrate. The solvent is preferably water and/or ethanol. The reducing agent is preferably ascorbic acid ($C_6H_8O_6$).

Preferably, the colloidal solution, when it comprises 100 parts by weight of oligodynamic metal, such as silver, and in particular silver nitrate, further comprises the corresponding relative amounts, i.e. relative to the oligodynamic metal, of 20-100 parts by weight of the hydrophilic polymer, and in particular PVP, and more preferably 50-100 parts by weight, and most preferably 75-85 parts by weight. Still further, the colloidal solution preferably comprises the corresponding relative amounts of 0.01-10 parts by weight of the reducing agent, and in particular ascorbic acid, and more preferably 0.1-1.0 parts by weight, and most preferably 0.3-0.7.

The coating may also comprise an osmolality-increasing compound, as is e.g. taught in EP 0 217 771. For example, the hydrophilic coating may contain an osmolality-increasing compound, for instance an inorganic salt selected from sodium and potassium chlorides, iodides, citrates and benzoates. Additionally or alternatively, it is also possible to provide the osmolality increasing compound in the wetting fluid.

Experimental Results 1

In a first line of experiments, catheters were prepared using a substrate material of a combination of the materials Polypropene, Polyethen Polyamide and Styren-ethen/butenstyren co-polymer, generally sold under the trade name Meliflex.

The substrates were coated with a hydrophilic coating. More specifically, a per se known coating process was used, in which isocyanate is used to form a polyurea network for binding PVP. More specifically, the coating according to the comparative example was prepared by dipping the substrates in a primer solution comprising a diisocyanate (named Desmodur IL), which is dissolved in methylene chloride to a concentration of 2% (weight/volume), for 15 seconds. The catheters were thereafter dried at ambient temperature for 60 seconds, and are then dipped for 3 seconds in a solution containing 7% (weight/volume) of polyvinylpyrrolidone (PVP K90) dissolved in methylene chloride. The catheters were then allowed to flush off at 35 deg. C. for 30 minutes, and then cured for 60 minutes at 80 deg. C., and were finally allowed to cool to room temperature and rinsed in water.

Thereafter, the coated catheters were dipped in colloidal solutions comprising colloidal silver particles. For this purpose, different colloidal solutions were used, having different concentrations of silver, colloidal silver particles of various sizes, etc. The catheters were dipped in the colloidal solution for 5 minutes, and were subsequently dried for 5 hours at 85 degrees C.

Subsequently, the catheter were packed and sterilized by radiation with a product dose of minimum 25 kGy.

The colloidal solution was prepared using different amounts of three different solutions, where said solutions were:

Solution 1: 0.009 g ascorbic acid in 500 ml demineralized water (0.1 mM)

Solution 2: 0.198 g AgNO3 in 580.5 ml demineralized water (2 mM)

Solution 3: 0.162 g PVP (K30) in 292.5 ml demineralized water (5 mM).

Solution 3 and solution 2 were first mixed together, and stirred and heated. When the combined solution reaches a certain temperature, a specified amount of solution 1 is added. For the preparation of the various colloidal solutions, solution 1 (0.1 mM) was added at different temperatures and with different quantities.

The concentration of colloidal silver particles and the size of the colloidal particles of the resulting colloidal solutions were calculated based on measurements with Ultravioletvisible spectroscopy. The degree of silver from the silver nitrate being transformed into colloidal particles were also calculated.

Antibacterial activity was tested with a method simulating a real use situation for urinary catheters. Hereby, the catheters were first wetted for 30 seconds in wetting liquid. Then, the catheters were dipped in a bacteria containing solution, simulating urine containing bacteria. More specifically, the solution contained Escherichia coli (E. coli) at a concentration of $10^3$ CFU/ml. CFU here stands for Colony Forming Units. Subsequently, the solutions in which catheters were dipped were incubated at 37 degrees C. for four hours, simulating the interval between catheterizations. The concentration of bacteria was then measured as CFU/ml and compared with the starting concentration.

In a first series of experiments, the colloidal solution was prepared using all (580.5 ml) of Solution 2, all (292.5 ml) of Solution 3, and 50 ml of Solution 1. As is presented in Table 1 below, Solution 1 was added at various temperatures:

TABLE 1

Variation of temperature when ascorbic acid is added

| Solution Example | Temperature | Colloidal particle size (diameter) | Number of colloidal particles | Degree of silver forming colloidal particles |
|---|---|---|---|---|
| A1 | Room temperature | — | — | — |
| A2 | Room temperature, and subsequent heating to 95° C. | 60 nm | 1.2E+11 | 20% |
| A3 | 60° C. | 90 nm | 1.2E+11 | 60% |
| A4 | 80° C. | 70 nm | 4.0E+11 | 90% |
| A5 | 90° C. | 60 nm | 6.5E+11 | 80% |
| A6 | 95° C. | 60 nm | 6.5E+11 | 85% |

From the measurements presented in Table 1, the following observations can be made:
- No colloidal silver particles are formed at room temperature.
- However, mixing of the solutions at room temperature and subsequent heating resulted in formation of colloidal particles.
  - The size of the colloidal particles were essentially the same for the solutions heated to 90 and 95 degrees C., regardless of whether the heating occurred prior to or subsequent to adding of the reducing agent (ascorbic acid).
- Heating to 80 degrees C. resulted in larger colloidal particles, and heating to 60 degrees C. resulted in still larger particles.
- Accordingly, it is concluded that lower temperatures generates larger particles, and that the resulting particle size may be controlled by controlling the temperature.
- Larger quantities of colloidal particles are formed at higher temperature than at lower temperatures.
- A significantly higher degree of the available silver forms colloidal particles when the heating occurs prior to addition of the reducing agent (ascorbic acid) than when heating occurs after the mixing.
- Higher mixing temperatures provide a higher degree of the available silver being formed into colloidal particles.

The antibacterial effect of all the solutions A2-A6 were tested on E. coli, and were found to have excellent antibacterial activity.

The solutions A3 and A5 were further used for preparation of catheters, in the process discussed above.

The water retention of the catheters were also tested after 1 minute and 6 minutes, respectively. The water retention was compared to catheters prepared in the above-discussed way, but without the additional step of dipping the catheters into any antibacterial solution. The result of these measurements were that all the catheters had sufficient water retention capacity. The water retention of the catheters dipped in Solution A3 was essentially equal to the reference catheters which had not been dipped in any antibacterial solution. The water retention of the catheters dipped in Solution A5 was slightly lower, but still sufficient for use as urinary catheters.

The antibacterial activity of the catheters were tested on E. coli. As a comparison, reference catheters which had not been dipped in antibacterial solution were tested. When the reference catheters were used, the concentration of bacteria increased from the initial about $1*10^3$ CFU/ml to $3.9*10^5$ in the solution (synthetic urine). When the catheters according to the invention, here the catheters dipped in Solution A3 and Solution A5, were used, the concentration of bacteria in the solution decreased from the initial about $10^3$ log CFU/ml to less than $10^1$ log CFU/ml (below detection limit). Accordingly, a significant antibacterial activity was obtained in the catheters prepared in accordance with the invention. Further, no difference in this respect was seen between the catheters prepared with Solution A3 and the catheters prepared with Solution A5.

Further, the total amount of silver in the catheters prepared with Solution A3 and A5, respectively, and the amount of silver released in synthetic urine and a phosphate buffer, respectively were analyzed. Here, the same catheters were first dipped in the phosphate buffer, simulating an initial activation/wetting step for the catheters, and thereafter dipped in synthetic urine, simulating the subsequent use of the catheters, when they are introduced into the urethra of the patient. The quantity of silver remaining on the catheter after use corresponds to the total quantity of silver before use, reduced with the amount of silver released in the phosphate buffer and the amount of silver released in the synthetic urine. The catheters were first dipped for 30 seconds in the phosphate buffer, which corresponds to a typical recommended wetting time for hydrophilic urinary catheters, and thereafter dipped in synthetic urine for 5 minutes, which corresponds to a typical duration of catheterization for intermittent urinary catheters. The results are presented in Table 2 below:

TABLE 2

Release of silver from catheters

| Catheter | Average total quantity of silver [µg/cm2] | Average amount of silver released in phosphate buffer [µg/cm2] | Average amount of silver released in synthetic urine [µg/cm2] |
|---|---|---|---|
| Solution A3 | 1.40 ± 0.04 | 0.30 ± 0.14 | 0.25 ± 0.11 |
| Solution A5 | 1.12 ± 0.19 | 0.45 ± 0.10 | 0.32 ± 0.10 |

From the measurements presented in Table 2, the following observations can be made:
- The total amount of silver in the catheters is higher for the catheters prepared with Solution A3.
- The release rate of silver is higher for the catheters prepared with Solution A5.
- A very high release rate of silver in both synthetic urine and phosphate buffer is obtained for both catheters.

In a second series of experiments, the colloidal solution was prepared using 580.5 ml of Solution 2, 292.5 ml of Solution 3, and various amounts of Solution 1 (se Table 3 below). Solution 1 was added at a temperature of 95° C.

TABLE 3

Variation of quantity of reducing agent (ascorbic acid) used

| Solution Example | Quantity of Solution 1 (ml) | Colloidal particle size (diameter) (nm) | Number of colloidal particles |
|---|---|---|---|
| B1 | 10 | 60 | Very few |
| B2 | 30 | 60 | 0.5E+11 |
| B3 | 50 | 60 | 6.5E+11 |
| B4 | 70 | 70 | 6.5E+11 |
| B5 | 90 | 80 | 6.5E+11 |

The calculation of the number of colloidal particles was made in accordance with the method proposed in the article "Light-Scattering Submicroscopic Particles as Highly Fluorscent Analogs and Their Use as Tracer Labels in Clinical and Biological Applications" of J. Yguerabide and E. Yguerabide, in Analytical Biochemistry 262, 157-176 (1988).

From the measurements presented in Table 3, the following observations can be made:

Use of larger quantities of ascorbic acid resulted in larger colloidal particles.

Accordingly, it is concluded that the resulting particle size may be controlled by controlling the amount of reducing agent (ascorbic acid) used.

Larger quantities of reducing agent (ascorbic acid) provide a higher degree of the available silver being formed into colloidal particles.

A significantly higher degree of the available silver forms colloidal particles when 50 ml or more of Solution 1 is used.

In conclusion, these experiments show that the size of the colloidal particles may be controlled by controlling the temperature of the synthesis procedure, and/or the amount of reducing agent being added. Further, it is clear that synthesis is possible even at relatively low temperatures. It is assumed that even lower temperatures than 60 degrees C. may be used. Lower temperatures provide a faster synthesis, which renders the production more cost-efficient.

Experimental Results 2

In a second line of experiments, the stabilization agent used above, i.e. PVP, which is the same hydrophilic polymer as used in the hydrophilic coating of the catheter, was tested against another commonly used stabilization agent, viz. poly acrylic acid (PAA).

The catheters were again prepared in the same way as discussed above under heading Experimental results 1.

Thereafter, the coated catheters were dipped in colloidal solutions comprising colloidal silver particles. For this purpose, different colloidal solutions were used, having been prepared using PVP and PAA, respectively.

Subsequently, the catheter were packed and sterilized by radiation with a product dose of minimum 25 kGy.

The colloidal solution C with PVP was prepared using:
Solution 1C, 0.0009 g ascorbic acid in 50 ml demineralized water (0.1 mM)
Solution 2C, 0.198 g AgNO3 in 580.5 ml demineralized water (2 mM)
Solution 3C, 0.162 g PVP (K30) in 292.5 ml demineralized water (5 mM).
Solution 3C and solution 2C were first mixed together, and stirred and heated.
When the combined solution had reached a temperature of 95 deg. C., the 50 ml of Solution 1C was added.

The colloidal solution D with PAA was prepared slightly differently, in order to be better suited for PAA, using:

Solution 1D: 0.0352 g ascorbic acid in 1000 ml demineralized water (0.2 mM)
Solution 2D: 0.034 g AgNO3 in 40 ml demineralized water (5 mM)
Solution 3D: 0.206 g PAA in 20 ml demineralized water (0.05M).
Solution 3D and solution 2D were first mixed together, and stirred and heated.
When the combined solution had reached a temperature of 97 deg. C., Solution 1D was added slowly, drop by drop.

With both the dipping in Solution C and Solution D, dipping times of both 5 minutes and 30 minutes were used.

As a reference, catheters prepared in the same way as discussed above, but without having been dipped in any antibacterial solution were used.

For the catheters prepared as discussed above, the antibacterial effect was tested, in the same way as discussed above under heading Experimental results 1. The results are presented in Table 4 below:

TABLE 4

Antibacterial activity with different stabilizing agents

| Catheter | End concentration log CFU/ml | Growth from start concentration |
|---|---|---|
| Reference | 5.71 ± 0.10 | 1.89 |
| Solution D (5 min) | 5.60 ± 0.21 | 1.77 |
| Solution D (30 min) | 5.40 ± 0.01 | 1.58 |
| Solution C (5 min) | 1.08 ± 0.15 | -2.85 |
| Solution C (30 min) | 1.00 ± 0.00 | -2.92 |

Further, for the same catheters, the total amount of silver and the amount of silver released in synthetic urine and a phosphate buffer, respectively were analyzed. Here, the same catheters were first dipped in the phosphate buffer, simulating an initial activation/wetting step for the catheters, and thereafter dipped in synthetic urine, simulating the subsequent use of the catheters, when they are introduced into the urethra of the patient. The quantity of silver remaining on the catheter after use corresponds to the total quantity of silver before use, reduced with the amount of silver released in the phosphate buffer and the amount of silver released in the synthetic urine. The catheters were first dipped for 30 seconds in the phosphate buffer, which corresponds to a typical recommended wetting time for hydrophilic urinary catheters, and thereafter dipped in synthetic urine for 5 minutes, which corresponds to a typical duration of catheterization for intermittent urinary catheters. The results are presented in Table 5 below:

TABLE 5

Release of silver from catheters

| Catheter | Average total quantity of silver [µg/cm2] | Average amount of silver released in phosphate buffer [µg/cm2] | Average amount of silver released in synthetic urine [µg/cm2] |
|---|---|---|---|
| Solution D (5 min) | 0.03 | 0.01 | 0.01 |
| Solution D (30 min) | 0.03 | 0.01 | 0.01 |
| Solution C (5 min) | 3.33 | 1.16 | 0.87 |
| Solution C (30 min) | 2.96 | 1.00 | 0.80 |

From the results presented in Tables 4 and 5, the following can be deduced:

The catheters prepared by use of Solution D, containing PAA, had very low amount of silver. Consequently, the release rate of silver from said catheters were also very low, and the antibacterial effect was hardly noticeable.

On the contrary, the solutions prepared in accordance with the invention, where the same hydrophilic polymer as used in the coating of the catheters was used as a stabilizing agent in the antibacterial solution, the amount of silver in the catheters were significantly better. Further, the release rate of silver from said catheters, as well as the antibacterial effect, was also significantly improved.

In addition, the catheters discussed above where tested in respect of water retention, and where found to have about equally good water retention capacity.

Experimental Results 3

In a third line of experiments, another type of coating was used. Here, the catheters were provided with a covalently crosslinked PVP coating.

The same catheter substrates as discussed above where used.

The coating of the catheters were provided by first dipping the catheter substrates in a solution comprising 1.5% urethane acrylate, 3% PVP and 0.18% irigacure, dissolved in 99.7% ethanol. The catheters were then dried and irradiated with UV radiation. The catheters were then dipped in a second solution, in which the colloidal silver particles were provided. The second solution comprised to ½ the antibacterial colloidal solution, and to ½ a coating forming solution. The coating forming solution comprised 5% PVP and 0.1% bensofenon, dissolved in 99.7% ethanol. The colloidal solution E was prepared with a solution comprising 0.3 mM ascorbic acid, a second solution comprising 1 mM $AgNO_3$, and a third solution comprising 1.3 mM PVP (K30). The preparation of the colloidal solution was made in the same way as discussed under Experimental results 2, with the only difference that ethanol was used as a solvent instead of water. After dipping in the second solution, the catheters were again dried and UV-irradiated. This resulted in a covalently crosslinked coating.

Subsequently, the catheter were packed and sterilized by radiation with a product dose of minimum 25 kGy.

As a reference, catheters prepared in the same way was used, but where the second dipping solution only contained the coating forming solution.

For the catheters prepared as discussed above, the antibacterial effect was tested, in the same way as discussed above under heading Experimental results 1. The results are presented in Table 6 below:

TABLE 6

Covalently crosslinked coating

| Catheter | End concentration log CFU/ml | Growth from start concentration |
|---|---|---|
| Reference | 4.93 ± 0.05 | 1.24 |
| Solution E | 2.71 ± 0.18 | −0.98 |

Further, for the same catheters, the total amount of silver was analyzed. The results are presented in Table 7 below:

TABLE 7

Release of silver from catheters

| Catheter | Average total quantity of silver [µg/cm2] |
|---|---|
| Solution E | 1.18 ± 0.36 |

From the results presented in Tables 6 and 7, the following can be deduced:

An adequate antibacterial effect is obtained also for catheters provided with a covalently crosslinked coating.

Experimental Results 4

For a fourth line of experiments, the antibacterial coating of the present invention was compared to two other types of antibacterial hydrophilic coatings.

For these experiments, all the catheters were prepared using the same substrate material as discussed above in relation to the previously discussed experiments.

As a comparative example (Comparative Example 1), the catheter substrates were first coated with an antibacterial coating. The coating was applied essentially as disclosed in U.S. Pat. No. 5,395,651 and U.S. Pat. No. 5,747,178. Accordingly, the substrates were first pre-treated with a chromic acid, and then activated by dipping the substrates in a dilute activation solution containing 0.01-0.2 grams per liter of a salt containing tin ions, dissolved in acidified demineralized water. After this treatment the substrates were rinsed in demineralized water. Thereafter, the substrates were dipped in a deposition solution comprising silver-containing salt, and more specifically silver nitrate, in an effective amount of no more than 0.10 grams per liter, a reduction agent and a deposition control agent. After deposition, the coated substrates were removed from the deposition solution and rinsed in demineralized water. Finally, the substrates were dipped in a stabilization solution comprising 0.001-0.1 grams per liter of salts of platinum and gold in a dilute acid. After stabilization treatment, the substrates were again rinsed in demineralized water, and subsequently dried.

On top of the antibacterial coating, a hydrophilic coating was applied, in the same way as discussed above under heading Experimental results 1, where isocyanate is used to form a polyurea network for binding PVP.

These catheters, prepared in accordance with Comparative Example 1, are here compared to the inventive examples prepared using Solutions C (5 min), C (30 min) and E, as discussed above.

For the catheters prepared as discussed above, the antibacterial effect was tested, in the same way as discussed above under heading Experimental results 1. The results are presented in Table 8 below:

TABLE 8

Comparison between different types of antibacterial coatings

| Catheter | Growth from start concentration |
|---|---|
| Comparative Example 1 | −2.34 |
| Solution C (5 min) | −2.85 |
| Solution C (30 min) | −2.92 |
| Solution E | −0.98 |

Further, for the same catheters, and also catheters prepared with Solutions A3 and A5, the total amount of silver and the amount of silver released in synthetic urine and a phosphate buffer, respectively were analyzed. As before, the same catheters were first dipped in the phosphate buffer, simulating an initial activation/wetting step for the catheters, and thereafter dipped in synthetic urine, simulating the subsequent use of the catheters, when they are introduced into the urethra of the patient. The quantity of silver remaining on the catheter after use corresponds to the total quantity of silver before use, reduced with the amount of silver released in the phosphate buffer and the amount of silver released in the synthetic urine. The catheters were first dipped for 30 seconds in the phosphate buffer, which corresponds to a typical recommended wetting time for hydrophilic urinary catheters, and thereafter dipped in synthetic urine for 5 minutes, which corresponds to a typical duration of catheterization for intermittent urinary catheters. The results are presented in Table 9 below:

TABLE 9

Further comparison between different types of antibacterial coatings

| Catheter | Average total quantity of silver [µg/cm2] | Average amount of silver released in phosphate buffer [µg/cm2] | Average amount of silver released in synthetic urine [µg/cm2] |
|---|---|---|---|
| Comparative Example 1 | 1.28 | 0.44 | 0.093 |
| Solution C (5 min) | 3.33 | 1.16 | 0.87 |
| Solution C (30 min) | 1.56 | 0.56 | 0.58 |
| Solution E | 1.12 | | |
| Solution A3 | 1.40 | 0.30 | 0.25 |
| Solution A5 | 1.12 | 0.45 | 0.32 |

Based on the data presented in Table 9, the following relative amounts of silver in the catheters before dipping, amount of silver released in the phosphate buffer, amount of silver released in the synthetic urine and amount of silver remaining in the catheters after dipping were calculated (Table 10 below):

TABLE 10

Further comparison between different types of antibacterial coatings

| Catheter | Relative quantity of silver in catheters before dipping | Relative quantity of silver released in phosphate buffer | Relative quantity of silver released in synthetic urine | Relative quantity of silver in catheters after dipping |
|---|---|---|---|---|
| Comparative Example 1 | 100% | 34% | 7% | 58% |
| Solution C (5 min) | 100% | 35% | 26% | 39% |
| Solution C (30 min) | 100% | 36% | 37% | 27% |
| Solution E | 100% | — | — | — |
| Solution A3 | 100% | 21% | 18% | 61% |
| Solution A5 | 100% | 40% | 29% | 31% |

From the results presented in Tables 8, 9 and 10, the following can be concluded:

The antibacterial activity of the catheters are sufficiently good for all the discussed alternatives.

However, the inventive examples prepared using a hydrophilic coating which forms a polyurea network show significantly better antibacterial activity than all the other examples.

The total amount of silver in the catheters prepared according to the invention are relatively low It is generally desired to have a low release of silver in the phosphate buffer, since this corresponds to the wetting step before use of the catheter. The release rate of silver in the phosphate buffer is essentially the same for all the tested catheters, except the catheter prepared with solution A3, which exhibits an exceptionally good (low) release rate in phosphate buffer.

Further, it is generally desired to have a high release rate of silver in the synthetic urine, since this corresponds to the release of silver in urine when the catheter is used for catheterization. All the catheters prepared in accordance with the invention have a significantly improved release rate of silver in the synthetic urine compared to the comparative example.

Consequently, the catheters prepared in accordance with the invention have the ability to release a substantial part of the oligodynamic metal where it is most useful and best needed—i.e. during the catheterization.

Further, it is generally desirable to have a low quantity of silver remaining in the catheter after use. Silver remaining in the catheters corresponds to silver not actively used for any useful antibacterial purpose. The catheters prepared in accordance with the present invention generally have a relatively low amount of silver remaining in the catheters after use (i.e. after the two dipping steps). This effect is particularly noticeable in the catheters prepared with solutions C and A (5 min).

Thus, the catheters prepared in accordance with the present invention have a release of silver from the catheter which is relatively high for all the inventive examples, and where the silver is also to a very large extent released where it is most useful.

Further, the inventive examples release a very high degree of the total amount of silver present in the catheters, which enables a catheter with good antibacterial effect and a relatively low production cost. The product hereby also becomes more environment friendly.

Accordingly, it can be concluded that the method of the present invention, which is comparatively simple and cost-effective compared to e.g. the methods of Comparative Example 1, still exhibits corresponding or even better properties in term of antibacterial activity, release rate and active use of the applied antibacterial metal.

CONCLUSION AND SUMMARY

The invention has now been discussed in relation to different embodiments. However, it should be appreciated by those versed in the art that several further alternatives are possible. For example, many other types of antibacterial coatings comprising oligodynamical metals may be used, as well as other types of hydrophilic coatings. It is further possible to use the invention for other types of catheters than urinary catheters, such as vascular catheters or the like, or for other types of medical devices having a hydrophilic coating.

It will be appreciated by those versed in the art that several such alternatives similar to those described above could be used without departing from the spirit of the invention, and all such modifications should be regarded as a part of the present invention, as defined in the appended claims.

The invention claimed is:

1. An intermittent urinary catheter with antibacterial activity, comprising a substrate material and a surface coating of a hydrophilic polymer arranged on at least a part of the surface of said substrate material, said hydrophilic polymer exhibiting a low friction when wetted, wherein said surface coating further comprises colloidal particles of an oligodynamic metal distributed within the hydrophilic polymer, wherein the size of the colloidal particles are 1-200 nm and wherein the colloidal particles comprises said oligodynamic metal and a hydrophilic polymer, the hydrophilic polymer hereby forming an encapsulating outer layer on each colloidal particle, thereby allowing a substantial part of the colloidal particles to be released during the first five minutes when inserted into the urethra, wherein the colloidal particles have been introduced into the surface coating after forming of the surface coating on the substrate.

2. The intermittent urinary catheter of claim 1, wherein the oligodynamic metal is silver.

3. The intermittent urinary catheter of claim 1, wherein the hydrophilic polymer is at least one of: polyvinyl compounds, polylactames, in particular such as polyvinyl pyrrolidones, polysaccharides, in particular heparin, dextran, xanthan gum, derivatised polysaccharides, hydroxyl propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxyl ethylmethyl acrylate, cationic copolymers of polyvinyl pyrrolidone and copolymer of polymethylvinyl ether and maleinic acid anhydride.

4. The intermittent urinary catheter of claim 1, wherein the hydrophilic polymer is polyvinyl pyrrolidone.

5. The intermittent urinary catheter of claim 1, wherein the hydrophilic polymer forms a polyvinylpyrrolidone-polyurea interpolymer coating, comprising a stable and non-reactive polyurea-network that binds the hydrophilic polyvinylpyrrolidone.

6. The intermittent urinary catheter of claim 1, wherein the hydrophilic polymer is cross-linked to said substrate material.

7. The intermittent urinary catheter of claim 1, wherein the colloidal particles are immersed into the hydrophilic polymer.

8. The intermittent urinary catheter of claim 1, wherein the colloidal particles are evenly distributed within the hydrophilic polymer.

9. The intermittent urinary catheter of claim 1, wherein the substrate material is made of a polymer material.

10. The intermittent urinary catheter of claim 1, wherein the substrate material comprises/is made of at least one of: polyurethanes, latex rubbers, silicon rubbers, other rubbers, polyvinylchloride, other vinyl polymers, polyesters, polyacrylates, polyamindes, polyolefins, thermoplastic elastomers, styrene block copolymers, or polyether block amide.

11. The intermittent urinary catheter of claim 1, wherein the substrate material is made of a blend comprising polyurethane(s), polyamide(s) and polyolefin(s).

12. The intermittent urinary catheter of claim 1 wherein the hydrophilic polymer further comprises an osmolality increasing compound.

13. The intermittent catheter of claim 1, wherein the colloidal particles comprises said oligodynamic metal and a hydrophilic polymer, said hydrophilic polymer forming the encapsulating outer layer on each particle is the same polymer as in the coating of the substrate material.

14. The intermittent catheter of claim 1, wherein the colloidal particles are loosely arranged within a previously formed hydrophilic coating.

15. The intermittent catheter of claim 1, wherein at least 18% of total amount of the colloidal particles are released during the first five minutes when inserted into the urethra, subsequent to wetting of the surface coating.

* * * * *